United States Patent [19]

Schaarschmidt

[11] Patent Number: 4,665,758
[45] Date of Patent: May 19, 1987

[54] SAMPLE TAKING DEVICE

[75] Inventor: Ulrich Schaarschmidt, Stutensee, Fed. Rep. of Germany

[73] Assignee: WAK Wiederaufarbeitungsanlage Karlsruhe Betriebsgesellschaft mbH, Eggenstein-Leopoldshafen, Fed. Rep. of Germany

[21] Appl. No.: 776,508

[22] Filed: Sep. 17, 1985

[30] Foreign Application Priority Data

Oct. 19, 1984 [DE] Fed. Rep. of Germany ....... 3438303

[51] Int. Cl.⁴ ............................................. G01N 1/10
[52] U.S. Cl. ................... 73/863.32; 141/130; 141/329; 73/864.23; 73/864.31
[58] Field of Search ............... 73/863, 864.23, 864.31, 73/864, 864.74, 864.51, 864.91, 863.32; 141/130, 329

[56] References Cited

U.S. PATENT DOCUMENTS

| | | | |
|---|---|---|---|
| 3,418,080 | 12/1968 | Rochte et al. | 73/864.23 X |
| 4,237,733 | 12/1980 | Kolb et al. | 73/864.23 X |
| 4,478,095 | 10/1984 | Bradley et al. | 73/864.23 X |
| 4,512,203 | 4/1985 | Calame-Lonjean et al. | 73/864.31 X |
| 4,516,436 | 5/1985 | Conche et al. | 73/864.31 X |

FOREIGN PATENT DOCUMENTS

| | | | |
|---|---|---|---|
| 2617594 | 11/1976 | Fed. Rep. of Germany | 73/864.23 |
| 712385 | 8/1966 | Italy | 73/864.23 |
| 463026 | 3/1975 | U.S.S.R. | 73/864.31 |

Primary Examiner—Stewart J. Levy
Assistant Examiner—Tom Noland
Attorney, Agent, or Firm—Spencer & Frank

[57] ABSTRACT

An apparatus for taking samples of a toxic or radioactive substance by introducing such substance into sample vessels, comprising a rotatable cylinder containing a recess movable between two positions for receiving a sample vessel; a needle head filling assembly disposed at the first position; a stripper located between the cylinder and the filling assembly for causing the filling assembly to disengage from the sample vessel during downward axial movement of the cylinder after filling; a housing which is open at the top, and a cover closing the top of the housing, with the cylinder, filling assembly and stripper being disposed in the housing, and the cover being provided with an opening above the needle filling assembly and dimensioned to permit passage of the filling assembly through the opening; a supply conduit for supplying substance to the filling assembly; and a support disc located in the housing and provided with a receiving bore for supporting the filling assembly while permitting the assembly to be removed from the receiving bore and withdrawn from the housing via the opening in the cover, the support disc having a fluid flow bore for placing the supply conduit in communication with the assembly.

7 Claims, 5 Drawing Figures 4,665,758

SAMPLE TAKING DEVICE

BACKGROUND OF THE INVENTION

The present invention relates to a sample taking device for toxic and/or radioactive substances, which device includes a needle head filling system for at least one sample vessel which can be moved toward the needle head filling system and toward an inlet and discharge conduit for the sample vessel by rotating and lifting movements which are imparted to a rotatable cylinder by means of a drive shaft. The needle head filling system and the inlet and outlet conduits are disposed above the rotary cylinder. Also, a stripper is provided with which the sample vessel, once it has been filled, is removed from the needle head filling system and held within the rotatable cylinder. Such a device is disclosed in copending, commonly-owned U.S. Ser. No. 672,180, filed by Schaarschmidt et al.

SUMMARY OF THE INVENTION

It is an object of the present invention to provide an improved sample taking device. More particularly, the improvements are with respect to the device's needle head function, radiation protection conditions and servicing of the components carrying the sample medium.

The above and other objects are achieved, according to the present invention, by a novel apparatus for taking samples of at least one of a toxic and radioactive substance by introducing such substance into sample vessels. The apparatus comprises:

a rotatable cylinder containing a recess for receiving such a sample vessel;

means including a drive shaft operatively coupled to the cylinder for imparting rotary and axial movements to the cylinder for moving the recess between first and second positions;

needle head filling means disposed above the cylinder at the first position of the recess for filling a sample vessel present in the recess with such substance, the cylinder being axially movable upwardly by the drive shaft for bringing the needle head filling means into engagement with the sample vessel during filling and being axially movable by the drive shaft downwardly for disengaging said needle head filling means from the sample vessel after filling;

stripper means located between the cylinder and the needle head filling means for causing the needle head filling means to disengage from the sample vessel during the downward axial movement of the cylinder after filling;

a housing which is open at the top, and a cover closing the top of the housing, with the cylinder, the needle head filling means and the stripper means being disposed in the housing, and the cover being provided with an opening above the needle head filling means and dimensioned to permit passage of the needle head filling means through the opening;

substance supply means including a supply conduit for supplying such substance to the needle head filling means;

a support disc located in the housing and provided with a receiving bore for supporting the needle head filling means while permitting the needle head filling means to be removed from the receiving bore and withdrawn from the housing via the opening in the cover, the support disc being further provided with a fluid flow bore located for placing the supply conduit in fluid flow communication with the needle head filling means; and vessel conveying means including a vessel transporting conduit having one end extending into the housing to a location associated with the second position of the recess.

Radiation protection is improved, according to the present invention, in that the sample bottle filling region with its gamma radiation shield forms a separate unit onto which the glove box, as the service and operating unit, is sealingly seated by means of screws or bolts. Since only the top side of the sample bottle filling mechanism need be accessible in the glove box, the glove box, including the gamma radiation shielded sample bottle filling mechanism disposed outside the box, becomes smaller and less expensive.

The static positioning of the drives by way of the drive shaft for the sample bottle filling device and its rods as used in the above-cited earlier application is replaced in the present invention by the glove box as the static element for positioning the drive mechanism.

Positioning of the needle head is improved in that a disc is provided with bores for introducing and discharging the sample medium. More particularly, the bores are congruent with the bores provided in the housing for introducing and discharging the sample medium, and with bores for accommodating the needle head and for the passage of the telescoping tube of the sample bottle transporting tube, is screwed to the housing by way of sealing face ground surfaces. This type of structural arrangement facilitates the use of needle heads equipped with dual needles and permits subsequent adjustment of the conical, ground needle head seats if there is damage.

Significant improvements in needle head function, radiation protection conditions and servicing of the components carrying the sample medium, particularly for solids-containing sample solutions, is realized with the introduction of a screen in the inlet bore of the needle head. With this simple measure, all built-in components for screen housing, rinse-back coupling and blocking member previously required at the sample inlet conduits toward the sample taking device are now eliminated. If solids or the like cover the screen, the needle head is drawn into the shielded transporting vessel and is cleaned in an ultrasonic bath. A rinsing adapter is introduced into the free needle head position with the aid of which preliminary and return conduits can be rinsed in the direction of the process vessel.

As a structural variation, the telescoping tube may be fastened directly to the stripper plate in the position reserved for sample bottle transport. If this measure is taken, a return spring can be omitted.

DESCRIPTION OF THE PREFERRED EMBODIMENTS

Figure 1:
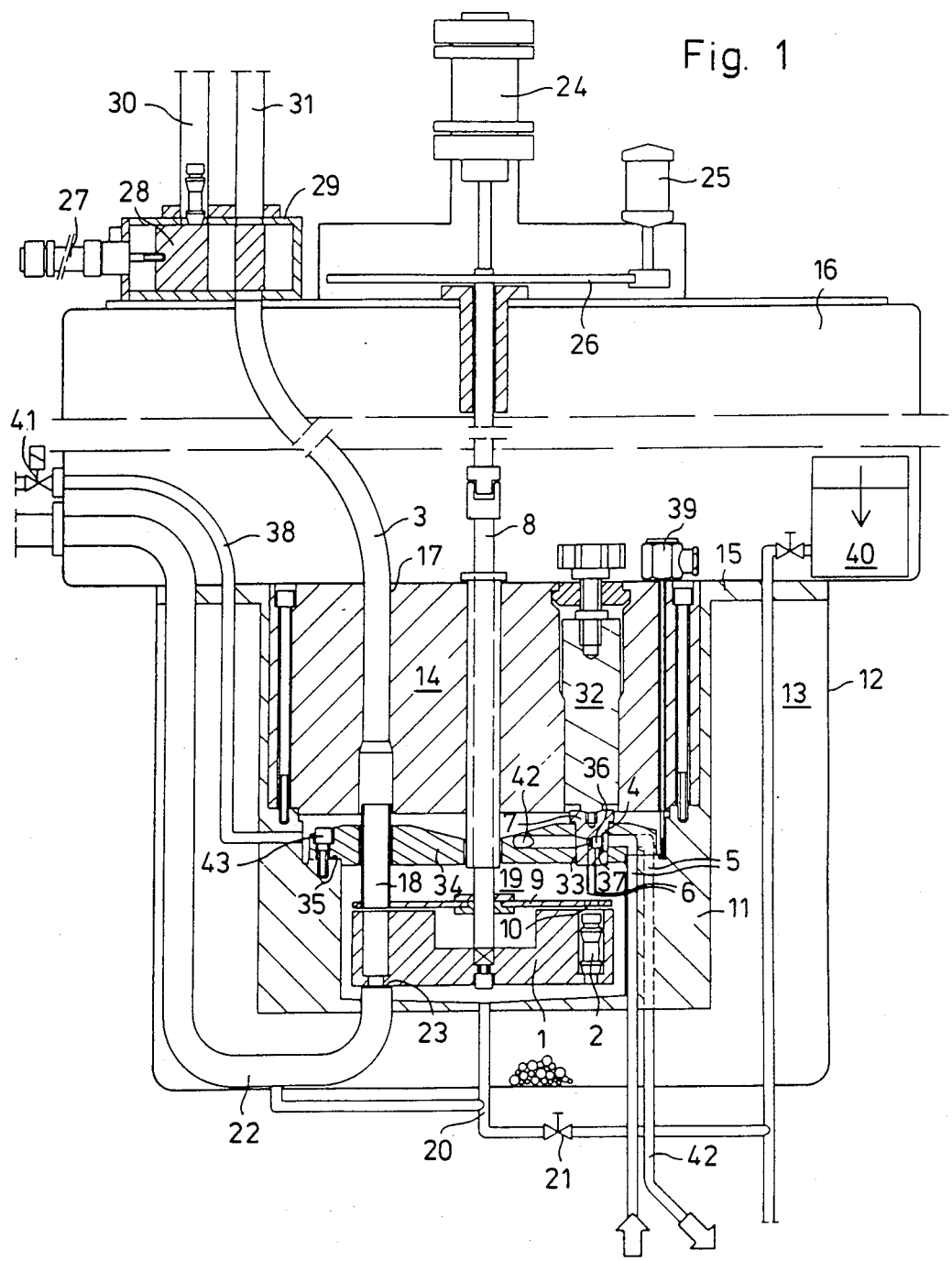
FIG. 1 is an elevational partly cross-sectional view of a preferred embodiment of the invention.
Figure 2:
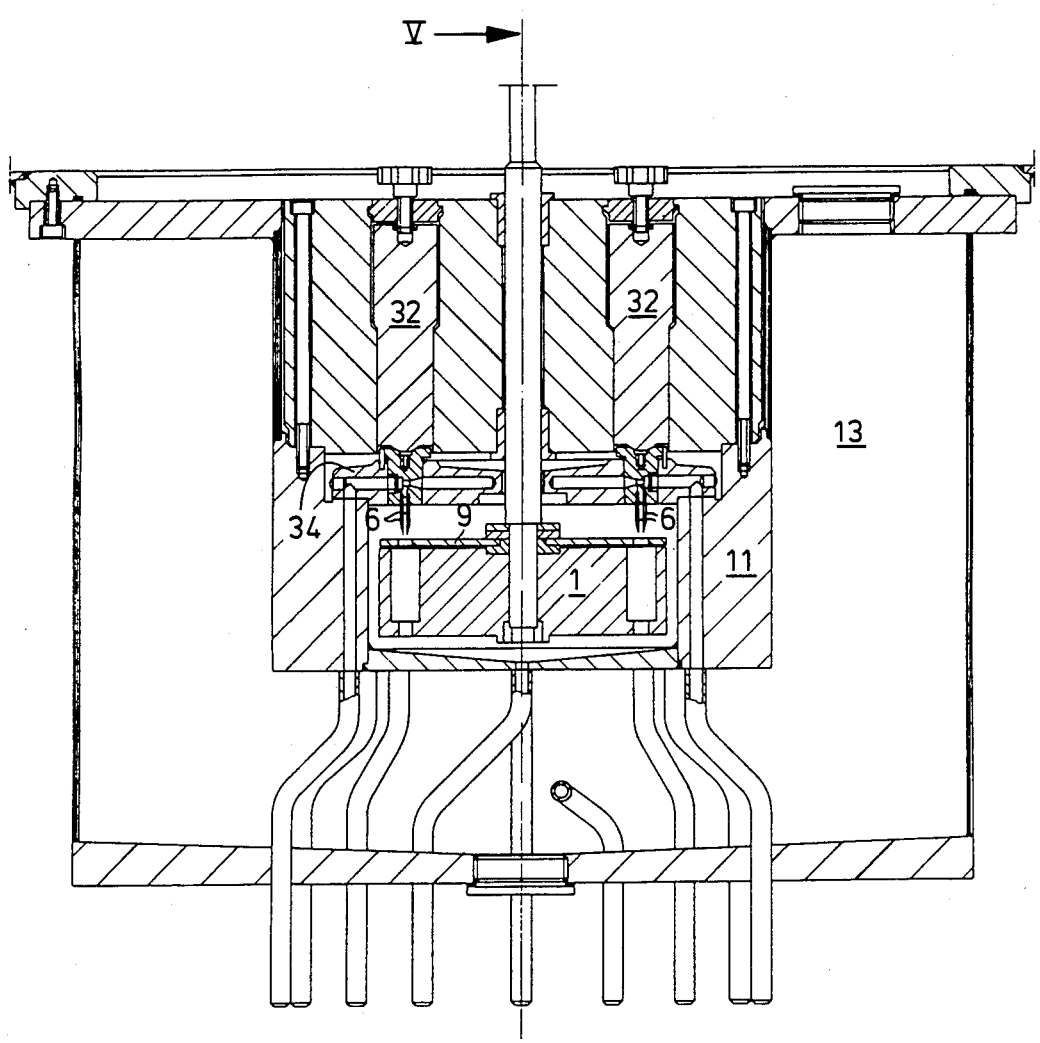
FIG. 2 is a cross-sectional view of part of the structure of FIG. 1.

Referring to FIG. 1, the illustrated device essentially includes a rotatable cylinder, or revolver head, 1 for holding and transporting one or a plurality of sample vessels 2 from a charging position below the open end of an inlet and outlet, or transporting, conduit 3 to the needle head filling system 4. The latter includes media inlet and outlet conduits 5 as well as two downwardly oriented hollow needles 6 fastened in needle head 7. Conduits 5 have a horizontal portion at the end connected to head 7.

Rotatable cylinder 1 is rotated into its various positions through a drive shaft 8 which can also at the same time raise and lower cylinder. The stroke of this movement is dimensioned in such a way that, sample vessel 2 (shown in the filling position in FIG. 1) can be displaced from below onto hollow needles 6. For this purpose, needles 6 as well as sample vessel 2 and the recess in rotatable cylinder 1 which accommodates vessel 2 are oriented parallel to the axis of drive shaft 8.

A stripper 9 which is secured against rotation, is likewise disposed at drive shaft 8 above rotatable cylinder 1 so as to be carried along during the lifting movements of cylinder 1, but not during its rotational movement. Stripper 9 is preferably a plate which, in the region of needle head filling system 4 is provided with openings 10 corresponding to, i.e. aligned with, needles 6. These openings permit passage of needles 6 for filling sample vessel 2. On the other hand, stripper 9 assures that sample vessel 2 is removed again from needles 6 when the filling process is completed and rotatable cylinder 1 is lowered back to its starting position.

Rotatable cylinder 1 and stripper 9 as well as needle head filling system 4 are disposed in a housing 11 which in turn is disposed in a sheet metal box 12 whose interior volume 13 is provided with shielding material. This shielding material can be in particulate form, as shown at the bottom of box 12 of FIG. 1. Media inlet and outlet conduits 5 lead through the bottom wall of box 12. Housing 11 has a shielding cover 14 and a circumferential flange 15, which together delimit and close the upper end of sheet metal box 12 which is firmly and tightly connected, e.g. screwed, to a glove box 16 disposed above it.

Drive shaft 8 passes through a passage or bore in shielding cover 14. Furthermore, inlet and outlet conduit 3 passes through another opening 17 in cover 14 to a location just above the upper surface of rotatable cylinder 1. Through a sleeve movable in conduit 3, the lower end of conduit 3 is configured as a telescoping conduit 18 so that the length of conduit 3 varies during the lifting movements of rotary cylinder 1. The lower end of conduit 18 is fastened on stripper plate 9 so that telescoping conduit 18 remains in the desired position in each respective case.

A dewatering conduit 20 equipped with a valve 21 is disposed at the bottom of housing 11 of the sample taking device. This bottom portion of housing 11 has the shape of a funnel. Located adjacent the side of housing 11 is a pneumatic air intake conduit 22. Conduit 22 extends through shielding box 12 and ends in an opening 23 at a location adjacent the bottom of rotatable cylinder 1 and located within interior 19 of housing 11 which is precisely below the open end of conduit 18. Conduit 22 is positioned this way so that, in the illustrated charging position of rotatable cylinder 1, the recess for receiving a sample vessel 2 is precisely aligned with both the open end of conduit 18 and opening 23 of conduit 22.

Housing 12 is fastened to box 16 which serves to hold the mechanisms for causing drive shaft 8 to perform rotating and lifting movements. These mechanisms include at least one lifing cylinder 24 for vertical lifting and a motor 25 for rotating shaft 8. For example, via a toothed wheel 26 can be employed with respect to which shaft 8 is rotationally fixed but axially movable. These mechanisms are seated outside of glove box 16. Drive shaft 8, inlet and outlet conduit 3 and pneumatic air intake conduit 22 are all brought through box 16 in a tightly sealed manner.

Transporting conduit 3 supplies the sample vessels 2 from an empty vessel magazine to the fill station. Conduit 3 also transports filled vessels pneumatically after filling leads to a positioning slide 28 disposed atop box 16. Slide 28 is provided with a vessel receiving passage and can be moved by means of a drive 27 in a tight miniature housing 29 located between a position in which the vessel receiving passage is below a delivery tube 30 of a device supplying sample vessels and a position in which that passage is above transporting tube 3. In the latter position, a continuous connection exists from the transporting tube 3 to a sample vessel pneumatic conveying conduit 31. In every other position of slide 28, the upper end of transporting tube 3 is tightly sealed.

Above needle head filling system 4, cover 14 is provided with a recess which can be closed by means of a corresponding plug 32. Upon removal of plug 32, needle head 7 and needles 6 can be pulled out toward the top or inserted into the conical receiving bore 33 of a needle head receiving disc 34 (see FIGS. 3, 4 and 5). Needle head receiving disc 34 is seated in a centered manner in the interior 19 of housing 11 on a circumferential edge 35 to which it is fastened by screws.

Drive shaft 8 as well as the sample vessel supplying and removing tube 3, or more precisely telescoping tube 18, pass through the corresponding recesses in disc 34. Receiving disc 34 is provided with bores 36 in such a manner that needles 6, when needle head 7 is inserted in disc 34, are able to communicate with sample inlet and outlet conduits 5.

In needle head 7 itself, in the region of bore 36, there is provided a screen 37 with which impurities are kept away from needles 6. After needle head 7 has been removed from needle head receiving disc 34 by means of plug 32, this screen 37 can be cleaned in an ultrasonic bath 40 in box 16 without it being necessary to dismantle the entire sample taking device. The interior 19 of housing 11 can be rinsed out via conduit 38 and conduit 20.

Figure 3:
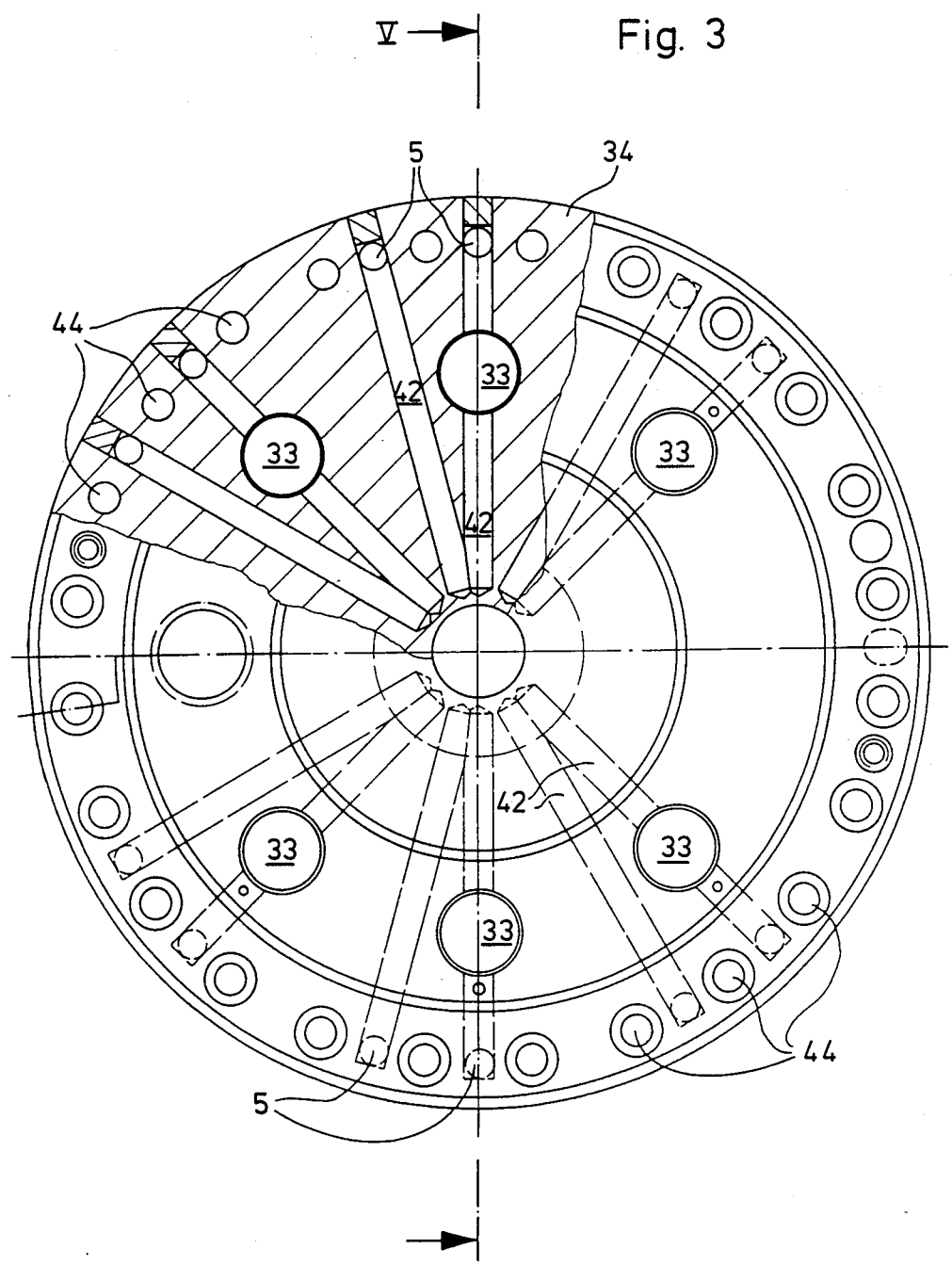
FIG. 3 shows a top view of the receiving disc.
Figure 4:
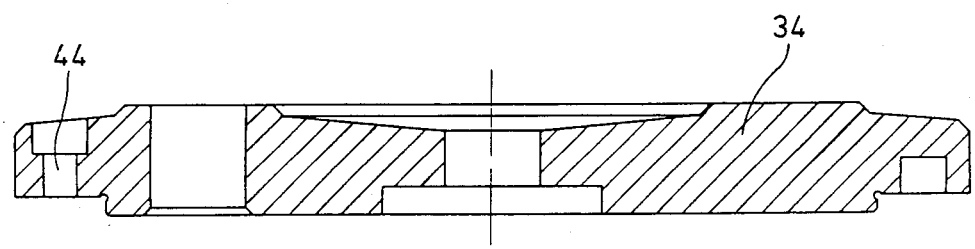
FIG. 4 and FIG. 5 show sectional views of the receiving disc of the present invention.
Figure 5:
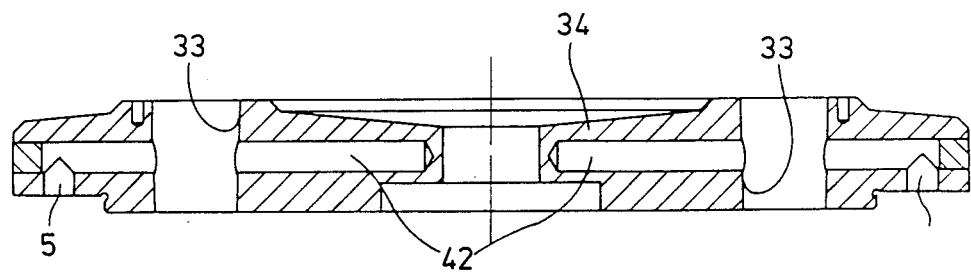

The communication between needle head 7 and the media inlet and outlet 5 is shown in FIGS. 3, 4 and 5. In FIG. 1, the sample outlet conduit is labeled 42 after it passes through the needle head. Only a bypass-stream of the solution flows through the sample vessel by the needles. The main flow passes directly through the venturi tube of the needle head to outlet conduit 42.

Based on the venturi tube effect, the produced differential pressure will force a flow through one needle and an exit flow through the second needle. The connections between needle heads 7 and the needles 6 are shown by FIGS. 2, 3, 4 and 5.

Referring to FIG. 1, the device 40 at the lower right-hand corner of box 16 is an ultrasonic equipment for cleaning needle heads.

Plug 32 is not connected to needle head 7, plug 32 presses the needle head 7 firmly into the conical bore 33. Plug 32 also serves as shield against radiation (see FIGS. 1 and 2). In order to change or to clean the needle heads 7, plug 32 will be withdrawn and the needle head removed by a thread bar, which can be screwed into a screw socket on the top of the needle head 7.

Through a bore in the shielding cover 14 an electrode 39 is installed. This electrode 39 controls the rinsing agent liquid level by operating the magnetic-valve 41 is of inlet conduit 38 which contains rinsing media. The outlet conduit 20 removes the rinsing media after having rinsed the interior 19.

Receiving disc 34 is best shown in FIGS. 3, 4 and 5. The surface of the housing 11 and opposite surface of the receiving disc 34 are both surfaces of metallic polish. Sealing will be provided by pressing together the surfaces by screws 43. The bores 44 for screws 43 are shown in FIGS. 3 and 4.

It will be understood that the above description of the present invention is susceptible to various modifications, changes and adaptations, and the same are intended to be comprehended within the meaning and range of equivalents of the appended claims.

What is claimed is:

1. An apparatus for taking samples of at least one of a toxic and radioactive substance by introducing such substance into sample vessels, comprising:
    a rotatable cylinder containing a recess for receiving such a sample vessel;
    means including a drive shaft operatively coupled to said cylinder for imparting rotary and axial movements to said cylinder for moving said recess between first and second positions;
    needle head filling means disposed above said cylinder at said first position of said recess for filling a sample vessel present in said recess with such substance, said cylinder being axially movable upwardly by said drive shaft for bringing said needle head filling means into engagement with such sample vessel during filling and being axially movable by said drive shaft downwardly for disengaging said needle head filling means from such sample vessel after filling;
    stripper means located between said cylinder and said needle head filling means for causing said needle head filling means to disengage from such sample vessel during the downward axial movement of said cylinder after filling;
    a housing which is open at the top, and a cover closing the top of said housing, with said cylinder, said needle head filling means and said stripper means being disposed in said housing, and said cover being provided with an opening above said needle head filling means and dimensioned to permit passage of said needle head filling means through said opening;
    substance supply means including a supply conduit for supplying such substance to said needle head filling means;
    a support disc located in said housing and provided with a receiving bore for supporting said needle head filling means while permitting said needle head filling means to be removed from said receiving bore and withdrawn from said housing via said opening in said cover, said support disc being further provided with a fluid flow bore located for placing said supply conduit in fluid flow communication with said needle head filling means; and
    vessel conveying means including a vessel transporting conduit having one end extending into said housing to a location associated with said second position of said recess.

2. Apparatus as defined in claim 1 further comprising a first box located above said housing, and a shielding box enclosing said housing and mechanically secured to said first box.

3. Apparatus as defined in claim 2 further comprising a screen for preventing passage of foreign particles disposed in said needle head filling system across the path of fluid flow through said supply conduit.

4. Apparatus as defined in claim 3 wherein said vessel transporting conduit comprises, at said one end, a telescoping conduit portion fastened to said stripper means.

5. Apparatus as defined in claim 2 wherein said vessel transporting conduit comprises, at said one end, a telescoping conduit portion fastened to said stripper means.

6. Apparatus as defined in claim 1 wherein said vessel transporting conduit comprises, at said one end, a telescoping conduit portion fastened to said stripper means.

7. Apparatus as defined in claim 1 further comprising a screen for preventing passage of foreign particles disposed in said needle head filling system across the path of fluid flow through said supply conduit.

* * * * *